(12) United States Patent
Heit et al.

(10) Patent No.: US 8,348,840 B2
(45) Date of Patent: Jan. 8, 2013

(54) DEVICE AND METHOD TO MONITOR, ASSESS AND IMPROVE QUALITY OF SLEEP

(75) Inventors: Juergen Heit, Pittsburgh, PA (US); Soundararajan Srinivasan, Munhall, PA (US); Diego Benitez, Pittsburgh, PA (US); Burton Warren Andrews, Pittsburgh, PA (US)

(73) Assignee: Robert Bosch GmbH, Stuttgart (DE)

( * ) Notice: Subject to any disclaimer, the term of this patent is extended or adjusted under 35 U.S.C. 154(b) by 245 days.

(21) Appl. No.: 12/700,079

(22) Filed: Feb. 4, 2010

(65) Prior Publication Data

US 2011/0190594 A1 Aug. 4, 2011

(51) Int. Cl.
*A61B 5/00* (2006.01)

(52) U.S. Cl. ........................................ 600/301; 600/300

(58) Field of Classification Search ........... 600/300–301
See application file for complete search history.

(56) References Cited

U.S. PATENT DOCUMENTS

| 5,544,649 | A | * | 8/1996 | David et al. ................... 600/301 |
| 5,605,151 | A | * | 2/1997 | Lynn ............................. 600/323 |
| 5,732,696 | A | | 3/1998 | Rapoport |
| 5,769,084 | A | | 6/1998 | Katz |
| 6,120,441 | A | | 9/2000 | Griebel |
| 6,392,962 | B1 | | 5/2002 | Wyatt |
| 6,425,861 | B1 | | 7/2002 | Haberland |
| 6,468,234 | B1 | | 10/2002 | Van Der Loos |
| 6,878,121 | B2 | | 4/2005 | Krausman |
| 6,993,380 | B1 | | 1/2006 | Modarres |
| 7,167,743 | B2 | | 1/2007 | Heruth |
| 7,309,314 | B2 | | 12/2007 | Grant |
| 7,366,572 | B2 | | 4/2008 | Heruth |
| 7,396,331 | B2 | | 7/2008 | Mack |
| 7,462,150 | B1 | * | 12/2008 | Bharmi ......................... 600/300 |
| 7,491,181 | B2 | | 2/2009 | Heruth |
| 7,572,225 | B2 | * | 8/2009 | Stahmann et al. ............ 600/484 |
| 7,654,948 | B2 | | 2/2010 | Kaplan |
| 8,002,553 | B2 | * | 8/2011 | Hatlestad et al. ............. 434/262 |
| 2004/0133081 | A1 | * | 7/2004 | Teller et al. ................... 600/300 |
| 2004/0244807 | A1 | * | 12/2004 | Sun et al. ...................... 128/904 |
| 2005/0042589 | A1 | * | 2/2005 | Hatlestad et al. ............. 434/262 |
| 2005/0124864 | A1 | * | 6/2005 | Mack et al. ................... 600/300 |
| 2005/0165323 | A1 | * | 7/2005 | Montgomery et al. ....... 600/544 |
| 2006/0019224 | A1 | | 1/2006 | Behar |
| 2006/0183980 | A1 | * | 8/2006 | Yang ............................. 600/301 |
| 2007/0096927 | A1 | * | 5/2007 | Albert ......................... 340/573.1 |
| 2007/0123758 | A1 | * | 5/2007 | Miesel et al. ................. 600/301 |
| 2008/0009685 | A1 | * | 1/2008 | Kim et al. ..................... 600/300 |
| 2008/0091122 | A1 | | 4/2008 | Dunlop |
| 2009/0005652 | A1 | * | 1/2009 | Kurtz ............................ 600/300 |

(Continued)

*Primary Examiner* — Henry M Johnson, III
*Assistant Examiner* — Bobby Soriano
(74) *Attorney, Agent, or Firm* — Taft Stettinius & Hollister LLP; Keith Swedo

(57) ABSTRACT

A medical sleep disorder arrangement integrates into current diagnosis and treatment procedures to enable a health care professional to diagnose and treat a plurality of subjects suffering from insomnia. The arrangement may include both environmental sensors and body-worn sensors that measure the environmental conditions and the condition of the individual patient. The data may be collected and processed to measure clinically relevant attributes of sleep quality automatically. These automatically determined measures, along with the original sensor data, may be aggregated and shared remotely with the health care professional. A communication apparatus enables the healthcare professional to remotely communicate with and further assess the patient and subsequently administer the treatment. Thus, a more accurate diagnosis and more effective treatment is provided while reducing the required clinician time per patient for treatment delivery.

20 Claims, 11 Drawing Sheets

U.S. PATENT DOCUMENTS

| | | | |
|---|---|---|---|
| 2009/0149721 A1* | 6/2009 | Yang | 600/301 |
| 2009/0203972 A1* | 8/2009 | Heneghan et al. | 600/301 |
| 2010/0049008 A1* | 2/2010 | Doherty et al. | 600/301 |
| 2010/0076333 A9* | 3/2010 | Burton et al. | 600/544 |
| 2010/0094103 A1* | 4/2010 | Kaplan et al. | 600/301 |
| 2010/0099954 A1* | 4/2010 | Dickinson et al. | 600/300 |
| 2010/0102971 A1* | 4/2010 | Virtanen et al. | 340/575 |
| 2011/0010014 A1* | 1/2011 | Oexman et al. | 700/276 |
| 2011/0112442 A1* | 5/2011 | Meger et al. | 600/595 |

* cited by examiner

| | Attribute | PIR motion | Acceleromet. | $CO_2$ | Light | Temp-Body | Temp-ENV | Air-flow | Humidity | Mic |
|---|---|---|---|---|---|---|---|---|---|---|
| 1 | Time of going to bed | X | | X | X | | | | | |
| 2 | Time of falling asleep (average) | | X | | | X | | | | |
| 3 | Time of waking up | | X | | | X | | | | |
| 4 | Time of getting up | X | X | | | | | | | |
| 5 | Time of actual sleep | | | | | | | | | |
| 6 | # times of falling asleep > 30min | | | | | | | | | |
| 7 | # times waking up at night or early morning | | X | | | X | X | | | |
| 8 | # times of getting up to use bathroom | X | X | | | X | X | | | |
| 9 | # times of uncomfortable breathing | | | | | | | X | | |
| 10 | # times of coughing or snoring loudly | | X | | | | | | | X |
| 11 | # times feeling too cold | | | | | X | | | | |
| 12 | # times feeling too hot | | | | | X | | | | |
| 13 | # times of having bad dreams | Manual input | | | | | | | | |
| 14 | # times of having pain | Manual input | | | | | | | | |
| 15 | Long pauses between breaths | | | | | | | X | | X |
| 16 | Twitching or jerking legs | | X | | | | | | | |
| 17 | Disorientation of confusion | Manual input | | | | | | | | |
| 18 | Subjective rating of sleep quality | Manual input | | | | | | | | |
| 19 | Trouble staying awake | Manual input | | | | | | | | |
| 20 | Enthusiasm getting things done | Manual input | | | | | | | | |
| 21 | Medicine taken | Manual input | | | | | | | | |
| | Additional (non-PSQI) attributes | | | | | | | | | |
| 22 | Light levels | | | | X | | | | | |
| 23 | Disturbances from other sound sources | | | | | | | | | X |
| 24 | Environmental sleep hygiene | | | X | X | | X | | X | X |
| 25 | Habitual sleep hygiene (eating, stimuli) | Manual input | | | | | | | | |

DEVICE AND METHOD TO MONITOR, ASSESS AND IMPROVE QUALITY OF SLEEP

BACKGROUND OF THE INVENTION

1. Field of the Invention

The present invention relates to systems and methods for improving sleep quality, and, more particularly, to systems and methods for electronically receiving and evaluating inputs related to people suffering from sleep disorders.

2. Description of the Related Art

More than forty million people living in the U.S. suffer from chronic, long-term sleep disorders. Because quality of sleep plays a major role in cognitive, physical and emotional well-being, these disorders have a significant negative effect on the quality of life of these individuals.

Sleep disorders are known to burden the U.S. health care system with approximately sixteen billion dollars in direct annual medical costs. The most prevalent sleep disorders are sleep apnea and insomnia. According to the National Institute of Health, about one in nine Americans suffer from sleep apnea, and about one in eight Americans suffer from chronic insomnia. If left untreated, subjects with chronic insomnia may experience the symptoms of their sleep disorder for decades, typically starting in young adulthood.

Chronic insomnia imposes a high burden on the health care system due to its high prevalence in the general population. There is little reliable data about the indirect costs that are caused by the increased number of accidents and reduced productivity due to chronic sleep disorders, but studies have shown that subjects suffering from undiagnosed insomnia spend approximately $1,000 more per person per year in direct medical expenses than do healthy subjects.

Subjects suffering from insomnia experience difficulty in initiating sleep, difficulty in maintaining sleep, or they wake up too early and find it difficult to go back to sleep. For a clinical diagnosis of insomnia, at least one of the above symptoms needs to be present. In addition, the symptoms or a combination of them must result in non-restorative or poor quality of sleep. Insomnia is classified as chronic if it persists for at least thirty days.

Chronic insomnia can be caused by substance abuse, mental disorders such as depression, breathing disorders, or by other sleep disorders such as periodic limb movement. Chronic insomnia can also be caused by the subject's life style and environmental factors resulting in poor sleep hygiene. Subjects are deemed to have poor sleep hygiene if they consume beverages with alcohol or caffeine, eat large meals, or engage in physically or mentally stimulating activity shortly before bed time. A highly variable bed time, or inadequate temperature, poor ventilation, noise or light within the sleep environment are also known to impact sleep hygiene negatively. Insomnia can also be a disease in itself, in which case it is not caused by another physical or mental condition.

For the diagnosis of a number of sleep disorders, polysomnography has become the gold standard. Polysomnography is a diagnostic procedure in a specially equipped laboratory or in a patient's home. During this procedure, numerous sensors are attached to the patient's body, and data is recorded for several hours or even for a whole night. The recorded data is interpreted by a sleep specialist. This provides the basis for the diagnosis of sleep disorders such as sleep apnea. Sleep apnea is a sleep disorder which is characterized by irregular breathing patterns while subjects are asleep. Among the typical sensor data acquired during polysomnography are: electroencephalogram, electro-oculogram, electromyogram at chin and tibalis, oxygen saturation, nasal and oral air flow, snoring via tracheal microphone, body position via gravity sensor, and abdominal and thoracic respiratory effort via induction plethysmography.

Unlike in the diagnosis of sleep apnea, polysomnography is not a standard instrument in the diagnosis of insomnia, and it is not indicated as a standard measure for therapy outcomes either. Only if sleep related breathing or periodic limb movement is suspected as the cause for insomnia, or if the previous treatment has failed, is polysomnographic evaluation in a sleep laboratory recommended. This is due to the high variability of sleep duration, sleep onset, and awakening in patients suffering from insomnia. Another factor is first night effects that cause some insomnia patients to sleep worse in a novel sleep environment, but patients suffering from psycho-physiological insomnia typically sleep better on their first night in the laboratory than they do at home. Common tools for the diagnosis of insomnia are self-reports, questionnaires, and sleep logs. Detailed questionnaires for the diagnosis of sleep disorders, such as the Pittsburgh Sleep Quality Index, have been developed, but clinical practitioners typically rely on less information and often require patients to record only the time they went to bed, the time they fell asleep, and the number of times they woke up during the night until the time they got up, at least one week prior to the first consultation.

Nowadays, clinicians depend on the patient's description of their symptoms. In the diagnosis of insomnia, patient self-reports concerning sleep quality play an important role. As sleep onset occurs unconsciously, there exists an intrinsic problem with the inaccuracy of self-reports concerning sleep quality. Patients tend to overestimate the lengths of time they are awake, and they generally underestimate the lengths of time they are asleep. Even though these reports are known to be inaccurate, they remain the basis for the diagnosis of insomnia to this day.

Clinicians also use reports of bed partners to determine whether or not certain sleep disorder symptoms are present that the patient may not be aware of Examples for these disorders are periodic limb movements or co-morbid sleep breathing disorders. For certain groups of the population, however, these reports cannot be obtained. Clinicians cannot get self-reports from infants or subjects with cognitive or mental disorders, such as dementia patients. For children, teenagers, young adults, singles, or seniors, a bed partner may not exist from whom to get information. In the evaluation of sleep hygiene, it is also important to determine to what extent environmental factors or personal habits negatively impact a patient's sleep quality. Examples of environmental factors causing poor sleep hygiene are improper ventilation, improper temperature, bright lighting, and high noise levels. Eliciting this information from patients during interviews poses additional challenges for clinicians.

The current options available for treatment of insomnia are pharmacological treatment, and cognitive behavior therapy. Pharmacologic treatment is the option most commonly chosen, even though it is known to have questionable long-term efficacy and it is associated with numerous side effects. Side effects of pharmacologic sleeping aids include memory impairments, altered sleep structure, risk of physical and psychological dependence, increased risk of falling and hip fracture for geriatric patients, and elevated risk of road accidents for elderly drivers. In addition, subjects suffering from a sleep breathing disorder and co-morbid insomnia must not take pharmacologic sleeping aids as they can prevent them from awakening enough to breathe. Thus, even though the symptoms of their sleep breathing disorder can be treated, these subjects will continue to suffer from their insomnia symptoms.

Non-pharmacological treatment, e.g., cognitive behavior treatment for insomnia (CBT) or psychotherapy, has been shown to improve quality of sleep in insomnia patients, and it achieves better long-term sleep improvements than pharmacological treatment. A typical CBT program combines education regarding sleep hygiene, stimulus control therapy, sleep restriction therapy, relaxation training, and cognitive therapy. Education regarding sleep hygiene teaches the patient how to avoid the factors mentioned above that can impact sleep quality negatively. Sleep restriction therapy is based on allotting a fixed time slot for lying in bed. The patient is prescribed to try to sleep only during this time period. Thus, the patient develops the habit of making more efficient use of the time in bed for sleep. Relaxation therapy is governed by light physical exercises that reduce tension in certain muscle groups, and training that reduces cognitive arousals. Finally, cognitive therapy corrects patients' misperceptions and fears regarding their need for sleep. Often insomniacs obsess about not being able to fall asleep, which raises tension and exacerbates insomnia. Administration of CBT typically takes eight weeks and up to ten therapist sessions of ninety minutes. Treatment cost due to required clinician time and availability of specialists experienced in CBT treatment inhibits widespread use of this non-pharmacological treatment option. CBT can reduce the severity of insomnia symptoms significantly, but demanding life events and bereavement may cause symptom relapse. For this reason, booster sessions of CBT are needed to help patients cope with relapse of symptoms especially in times of physical or psychological distress. Current therapy regimen, however, provide no means for intervention when patients are at risk for relapse or when their compliance declines.

Most subjects suffering from insomnia discuss the symptoms of their sleep disorder with their primary car physician (PCP) first. The PCP can prescribe pharmacological sleeping aids if other health problems can be excluded. Otherwise, the PCP may refer the patient to a sleep specialist who will require the patient to fill out a sleep diary and questionnaires before the first consultation. The questionnaires are used to screen for physical and mental health problems. In the sleep diary, the patient is supposed to log times of going to bed, times of awakening during the night and in the morning, and times of rising. Most specialists also require patients to log their intake of medication and other substances such as alcoholic or caffeinated beverages. Most commonly, sleep aids are prescribed if the sleep specialist can exclude other sleep disorders, e.g., sleep breathing disorders and mental disorders. The patient's self-reports consisting of the filled out questionnaires and sleep diaries are the basis of the specialist's evaluation, but a sleep study may be required to gain certainty as to the absence of other sleep disorders.

What is neither disclosed nor suggested in the art is a system and method for monitoring, assessing and improving a patient's sleep quality that overcomes the problems and limitations described above.

SUMMARY OF THE INVENTION

The present invention may provide a medical device and method assisting with and integrating into current diagnosis and treatment procedures. More particularly, the invention may enable a health care professional experienced in sleep medicine to diagnose and treat a plurality of subjects suffering from insomnia. The invention may address the needs for accurate diagnosis and more effective treatment while reducing the required clinician time per patient for treatment delivery.

In one embodiment, the system of the invention may enable clinicians to rule out other sleep disorders and initiate delivery of Cognitive Behavior Treatment. In another embodiment the system may perform diagnosis and initiate treatment autonomously or automatically. Both embodiments may extricate or relieve clinicians from treatment delivery and allow them to focus on supervision of patient compliance and treatment response. As a result, the amount of required clinician time and consequently the treatment cost per patient is significantly reduced. As treatment is performed remotely, the patient may be freed of dependence on the local availability of sleep specialists. Moreover, sleep specialists may reach a greater number of patients by using the system.

In one embodiment, a system front-end may determine on a nightly basis how well a patient sleeps and which patient behaviors and which environmental and body conditions affect sleep quality. This information may be stored in a remote database. By virtue of the information in this database, clinicians can review sleep quality of their patients for any given night at a time of the clinician's choosing. This mechanism may enable a novel treatment method: Instead of monitoring and delivering treatment in real-time (e.g., via video while the patient is sleeping), clinicians may need only to adjust the parameters of the treatment which is automatically delivered by the system front-end.

The invention comprises, in one form thereof, an arrangement for monitoring a patient's sleep activity. At least one environmental sensor senses a condition of an environment for sleeping. At least one body-worn sensor is worn by the patient during the sleep activity and senses a condition of the patient during the sleep activity. A first communication apparatus includes a first camera, first microphone, first audio speaker and first video display disposed proximate to at least one of the sensors. A second communication apparatus includes a second camera, second microphone, second audio speaker and second video display disposed at a location remote from the first communication apparatus. A first processing means is communicatively coupled to the environmental sensor, the body-worn sensor, and to the first communication apparatus. The first processing means collects and aggregates sensor readings from the environmental sensor and from the body-worn sensor; prepares a report based on the aggregated sensor readings; receives output signals from the first microphone and the first camera; provides a first audio signal played on the second audio speaker and at least partially based on the output signal from the first microphone; and provides a first video signal displayed on the second video display and at least partially based on the output signal from the first camera and on the report. A first means for transmitting the report, the first audio signal and the first video signal to the remote location is communicatively coupled to the first processing means. A second processing means is communicatively coupled to the second communication apparatus. The second processing means receives output signals from the second microphone and the second camera; provides a second audio signal played on the first audio speaker and at least partially based on the output signal from the second microphone; and provides a second video signal displayed on the first video display and at least partially based on the output signal from the second camera. Second means for transmitting the second audio signal and the second video signal to the first processing means is communicatively coupled to the second processing means.

The invention comprises, in yet another form thereof, an arrangement for treating a patient having a sleep disorder. At least one environmental sensor senses a condition of an environment for sleeping. At least one body-worn sensor is worn by the patient during the sleep activity and senses a condition of the patient during the sleep activity. A tactile actuator is worn by the patient. A first communication apparatus includes a first camera, first microphone, first audio speaker and first video display. A second communication apparatus includes a second camera, second microphone, second audio speaker, second video display and keyboard. The second communication apparatus is disposed at a location remote from the first communication apparatus. A first processing means is communicatively coupled to the environmental sensor, the body-worn sensor, the tactile actuator, and to the first communication apparatus. The first processing means collects sensor readings from the environmental sensor and from the body-worn sensor; receives output signals from the first microphone and the first camera; provides a first audio signal played on the second audio speaker and at least partially based on the output signal from the first microphone; and provides a first video signal displayed on the second video display and at least partially based on the output signal from the first camera. A first transmitting means transmits the first audio signal and the first video signal to the remote location. The first transmitting means is communicatively coupled to the first processing means. A second processing means is communicatively coupled to the second communication apparatus. The second processing means receives output signals from the second microphone, the second camera, and from the keyboard; provides a second audio signal played on the first audio speaker and at least partially based on the output signal from the second microphone; provides a second video signal displayed on the first video display and at least partially based on the output signal from the second camera; and provides a tactile signal controlling the tactile actuator. A second means transmits the second audio signal, the second video signal, and the tactile signal to the first processing means. The second transmitting means is communicatively coupled to the second processing means. An image displayed on the second video display is dependent upon the sensor readings.

An advantage of the present invention is that the same measures or measurements may be taken during diagnosis and treatment. As the system measures attributes of sleep quality uniformly and accurately, clinicians may obtain objective measures of a patient's response to treatment. CBT consists of multiple components. Objective measures concerning treatment response may enable adaptation of treatment protocol to maximize individual convalescence.

Another advantage is that the invention may replace self-reporting with objective assessment of sensor data. The unique set of sensors and automatic classification of nightly events and attributes affecting sleep hygiene may provide a more accurate and objective means to clinicians than do patient self-reports. The automated classification may also release patients from the burden of having to fill out self-reports. In this way, patients who are not able to provide self-reports (e.g., infants or patients with cognitive impairments or mental disabilities) can be reached as well. This advantage may be enabled by automatic classification and quantification of sleep quality attributes.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 7 is a table showing the sensor data/manual inputs that may be used to quantify each sleep quality attribute, according to one embodiment of the invention.

Figure 1:
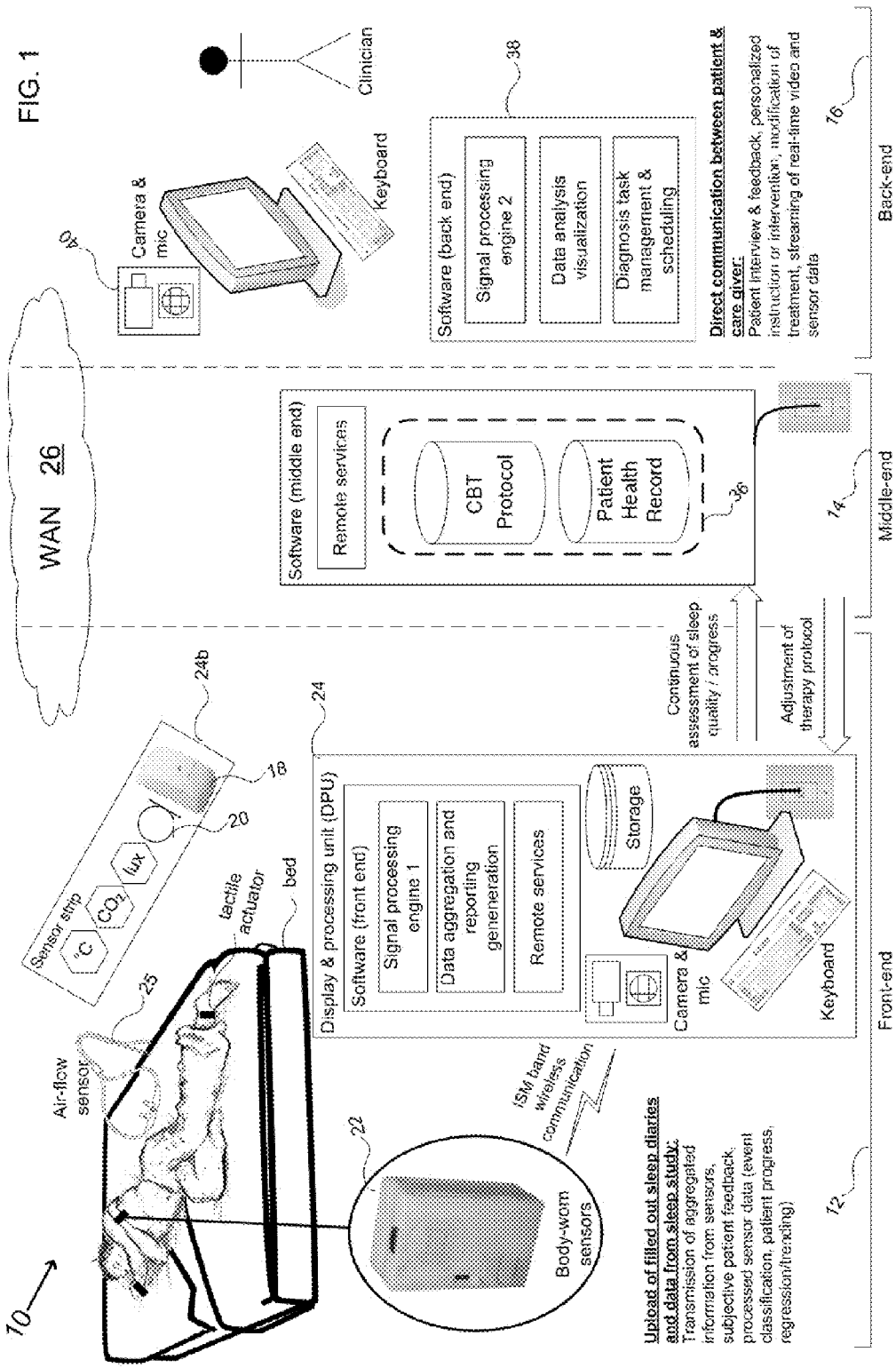
FIG. 1 is a block diagram of one embodiment of a sleep disorder monitoring, diagnostics, and treatment system of the present invention.
Figure 2:
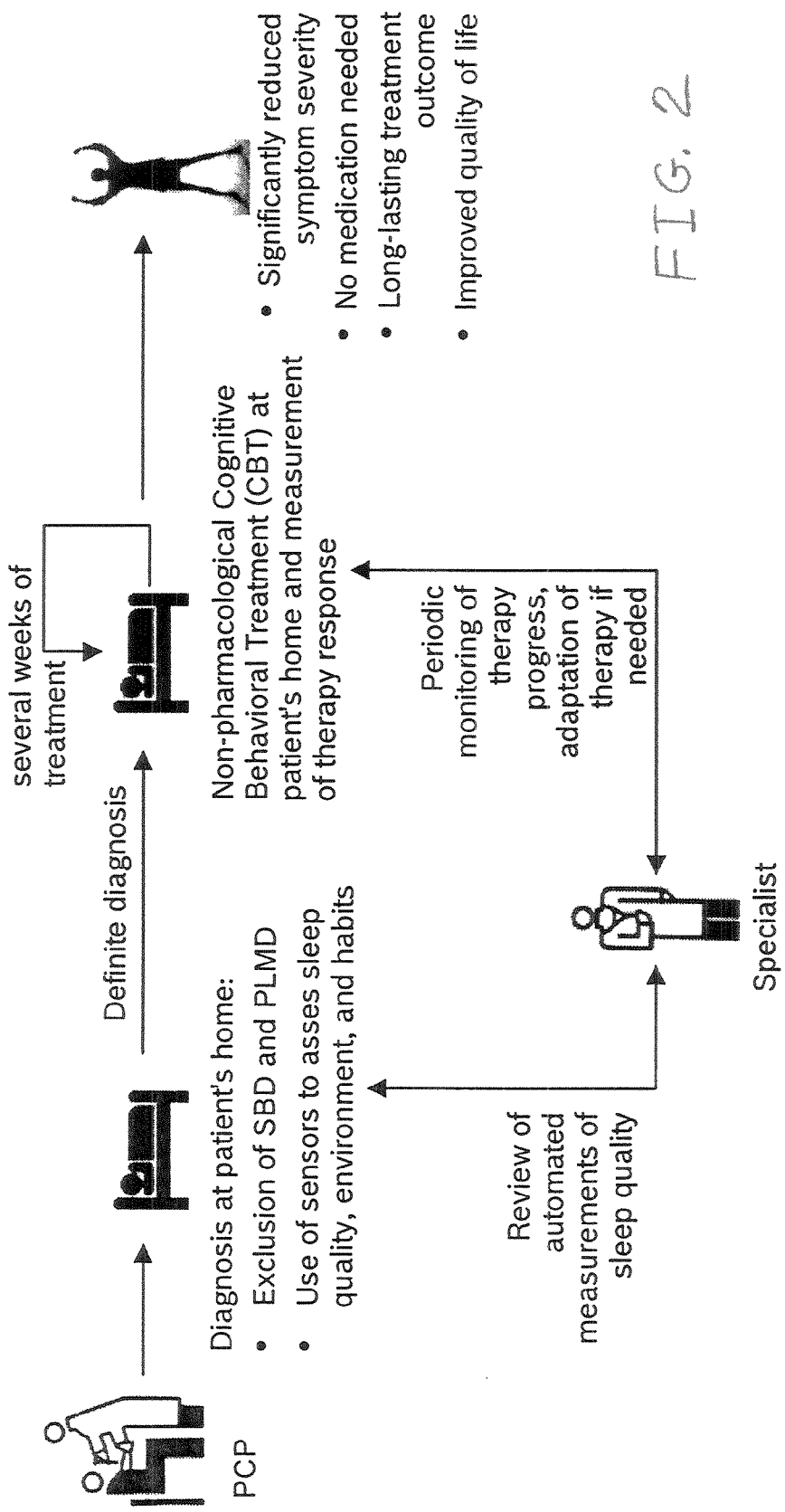
FIG. 2 is a flow diagram of one embodiment of a diagnosis and treatment procedure of the invention.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and made part of this disclosure.

A. Procedure to Assess and Improve Quality of Sleep

Referring now to the drawings, and particularly to FIG. 1, there is shown one embodiment of a sleep disorder monitoring, assessment, and treatment system 10 of the present invention including a front end 12, a middle end 14, and a back end 16. System 10 may supplement and integrate into current procedures of sleep disorder diagnosis and treatment. System 10 may enable an efficient procedure, outlined in FIG.

2, for diagnosis and treatment of insomnia. After an initial assessment of the patient's physical and mental health by their PCP, subjects who are suspected of suffering from insomnia are prescribed to use system 10. Front end 12 of system 10 may include sensors such as a motion sensor 18 and microphone 20 deployed in the patient's sleep environment as well as sensors 22 that may be worn on the patient's body. Sensors 18, 20, 22 may be used to assess the patient's sleep quality and to screen for other sleep disorders. Initially, system 10 may screen for sleep breathing disorders (SBD) and periodic limb movement disorder (PLMD). Several attributes of sleep quality may be determined on a nightly basis. All data collected and processed by system 10 can be reviewed remotely by sleep specialists at a time of their choosing. System 10 may also automatically generate summarizing reports to give the specialist a quick overview of the data. The data may be reviewed by the specialist and may provide the basis for diagnosis.

With regard to system facilitation of diagnosis and treatment, the sleep specialist interacts with monitoring system 10, and, more specifically, with back-end 16. If a sleep breathing disorder is diagnosed by the sleep specialist, he may initiate a separate treatment of the disorder. After that, the specialist may use the system to monitor sleep quality to identify whether or not the patient still experiences symptoms of insomnia. In order to treat insomnia symptoms, the specialist can initiate non-pharmacological cognitive behavior treatment at the patient's home. During the time of treatment, monitoring for efficacy continues, and the specialist can monitor the patient's therapy response periodically. Since CBT consists of multiple components, individuals may respond differently to particular components of the therapy. The sleep specialist can then adapt or modify the therapy to the individual, if needed. System 10 may facilitate such individual adaptation by providing appropriate user interfaces, which are described hereinbelow. Individual adaptation may have the potential to improve average treatment outcomes.

An advantage of using system 10 is a reduction in time a clinician needs to devote to a patient. This reduction may be due to the sleep specialist now needing only to monitor treatment outcome, but not having to deliver the treatment himself. Reduced clinician time may translate into reduced treatment cost. Reduced clinician time per patient and decreased treatment cost may improve availability of this type of treatment to subjects suffering from insomnia.

B. System Front-End

Figure 3:
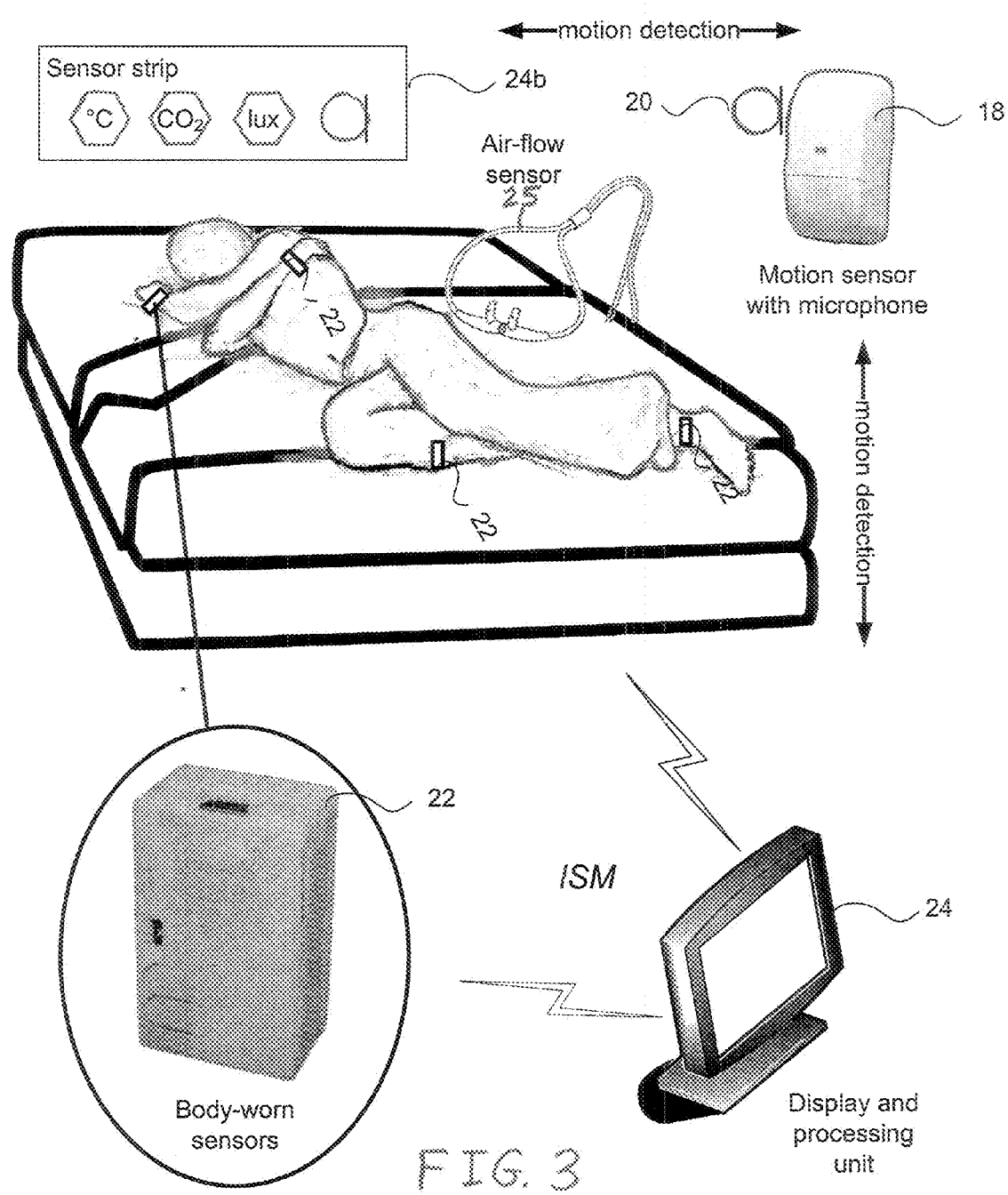
FIG. 3 is a block diagram of sensors included in the front end of the system of FIG. 1.

Front end 12 may be deployed in a patient's sleep environment. In one embodiment illustrated in FIGS. 1 and 3, front end 12 may include a display and processing unit (DPU) 24, two passive infrared motion sensors 18, microphones 20, one or more body-worn motion sensors 22, temperature sensors, a light sensor, and a carbon dioxide ($CO_2$) sensor on a sensor strip 24b, a humidity sensor, a vibration sensor, a barometric pressure sensor, and a body-worn airflow sensor 25. Operation of front end 12 may involve sensor data acquisition, automatic classification of parameters of sleep quality, and user interaction. In other embodiments, front end 12 may include one or more pressure sensors, infrared cameras, and radar-based sensors. In yet other embodiments, front end 12 may include a body-worn vibration producing device that vibrates such that a patient is woken from sleep by the vibration at a certain time and/or is prompted to get out of bed at a certain time. Front end 12 may alternatively include another form of tactile actuator that is capable of providing a noticeable tactile sensation to the patient. Individuals skilled in the art may appreciate that both temperature sensors and tactile actuator may be integrated into body worn sensor 22.

DPU 24 may aggregate and process sensor data. DPU 24 may be a special purpose computer programmed to perform the tasks described in this section, but it is also possible that DPU 24 may be a general purpose computer that allows for the use of the sensors described above. In one embodiment, the sensors send data to the display and processing unit by use of wireless communication in the industrial, scientific and medical (ISM) band. DPU 24 may be set up in an environment that is conducive for cognitive behavior treatment of the patient, but may be excluded from the sleep environment of the patient, where it could negatively affect sleep hygiene. DPU 24 may run software that extracts features from the sensor data in the time domain and in the frequency domain to automatically classify events that occur from the time the patient goes to bed until the time the patient rises in the morning. The software running on DPU 24 may aggregate this information into reports that may be used by the clinician for diagnosis and to evaluate treatment progress. The report may include not just sensor data, but also actual sleep quality attributes that have been determined from the raw sensor data using mathematical models. The data from the sensors may be first processed in order to automatically quantify clinically relevant attributes of sleep quality, and then the sensor data may be collected, aggregated, and shared remotely with the health care professional.

When connected to a Wide Area Network (WAN) 26 (FIG. 1), the patient can remotely consult his therapist by means of a built-in camera and microphone. DPU 24 may be used to instruct the patient in setting up the system and in the use of the sensors mentioned above. Delivery of treatment may be done mostly by standardized content stored on DPU 24. This content may include, but is not limited to, audio-visual instructions as well as interactive educational and motivational information stored in text form. Depending on therapy progress, the clinician may change this content or add to the content. The clinician may, for example, change the frequency, the duration, and the succession of particular exercises of CBT, or hold real-time therapy sessions with the patient using the remote audio/video conferencing capabilities of the system. As clinicians may observe symptoms and therapy progress by virtue of increased or decreased measures of sleep quality for the individual patient, clinicians may not need to monitor patients during their sleep activity in real-time. The data acquired in real-time can be stored for future analysis or reference, however. For the parts of CBT that can be taught to the patient interactively, the patient may get real-time feedback from DPU 24.

Passive infra red (PIR) motion sensors 18 may be statically mounted and may detect both horizontal and vertical movements of human subjects lying in bed. Sensors 18 may be used to identify when a person gets in and out of bed. PIR motion sensors 18 may be referred to herein as mounted motion sensors.

Body worn sensors 22 may be worn on the patient's non-dominant wrist and on both left and right ankles, among other locations on the patient's body. Sensors 22 may acquire data related to human motion. Sensors 22 may measure the intensity of motion as well as identify the type of motion.

By use of the above-described sensors, system 10, and more specifically front end 12, in at least one embodiment, may determine the time of sleep on-set, the time of sleep duration, the lengths of time spent awake after sleep on-set, the time of awakening, the time of getting up, and the times of periodic limb movements. In one embodiment, each sensor node may include at least one Micro-Electro-Mechanical Systems (MEMS) three-dimensional inertial sensor. Temperature sensors in the body worn sensor nodes, for example, may be used to acquire the subject's body temperature and to estimate circadian rhythms, and/or may be used to identify whether the patient is too hot or too cold. The use of inertial sensors to analyze activity levels of human subjects may be extended to the characterization of circadian rhythm patterns or sleep disturbances in people with insomnia. The use of both body-worn and mounted motion sensors may enable distinguishing between movements of the patient and movements of a bed partner. These sensors may also be used to identify sleep walking During diagnosis, there may be a special need for the sensors worn on the ankles to determine whether or not periodic leg movement causes the patient's insomnia.

Microphones 20 may be used to identify and record environmental noises that are disruptive to sleep as well as snoring of the patient or of the bed partner. Having at least two microphones at different locations may enable the system to approximate the location of the sound source. This may enable differentiating between sounds originating from the patient, sounds originating from the bed partner, and environmental noise. In one embodiment, the microphones may be integrated into the mounted motion sensors.

In order to assess sleep hygiene, environmental sensors for light, temperature, vibration, barometric pressure, and $CO_2$ may be used. In one embodiment, these sensors are integrated into a separate or detachable hardware module which sends its data wirelessly to DPU 24. In one embodiment, a vibration sensor is coupled to the patient's bed in order to sense vibration caused by the building's HVAC system, audio systems near the building, and other sources of building vibration. The vibration sensor may be a microphone able to pick up very low frequencies.

Figure 4:
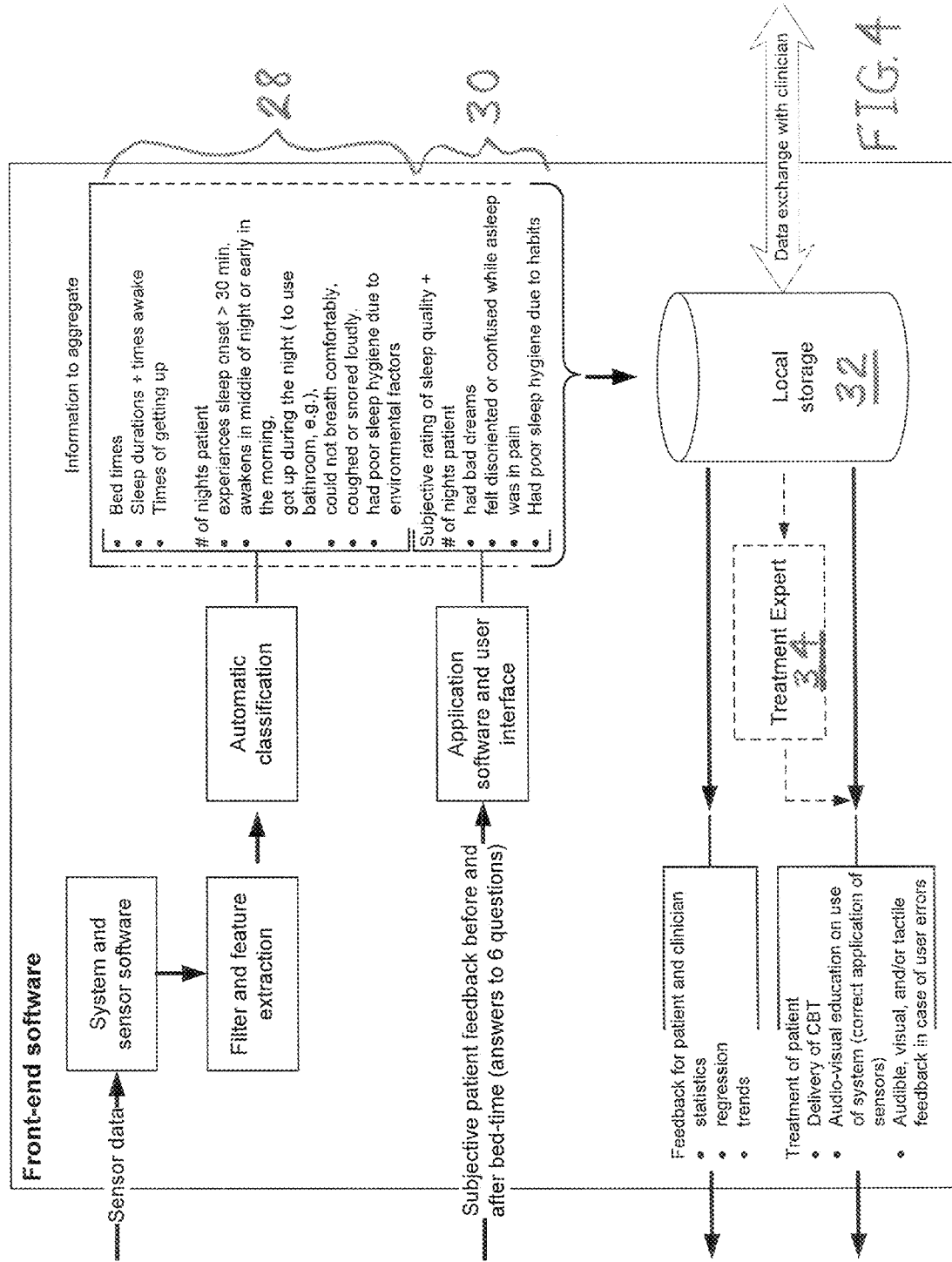
FIG. 4 is a block diagram of one embodiment of software included in the front end of the system of FIG. 1.

For diagnosis and treatment of insomnia, DPU 24 may collect information on a daily basis. The information collected may include data collected before, during, and after the patient's bed time to provide a comprehensive picture of the patient's sleep quality. The block diagram of FIG. 4 shows the data flow of the collected information from the perspective of the software of front end 12.

Each night, front end 12 may classify activities automatically. Front end 12 may aggregate this information and fill out a self report questionnaire. While it is possible for a tailored particular questionnaire to be determined by the clinician, in one embodiment the Pittsburgh Sleep Quality Index (PSQI) may be used to report objective, quantifiable information, as well as subjective perceptions of sleep quality, from a patient to a clinician. The information that may be automatically determined by DPU 24 may include the time that the patient went to bed; the lengths of time the patient was awake in bed; the number of minutes the patient was in bed until he fell asleep; the time at which the patient got up; the lengths of time the patient was asleep; the times at which the patient woke up during the night; the times at which the patient got up out of bed during the night; the patient's breathing pattern (e.g., to determine whether or not the breathing is irregular); the degree to which the patient coughs and snores; the degree to which the patient experiences leg twitching and jerking; the degree to which the patient makes other restless movements; light levels; noise levels; $CO_2$ saturation of the air in the sleep environment; humidity; temperature (body and environment); and barometric pressure.

DPU 24 may calculate sleep parameters or measurements that are composed by, or derived from, those measures listed above. For example, DPU 24 may calculate the patient's sleep efficiency, which may be defined as the ratio of time spent asleep to the time spent in bed.

Data from the sensors described above as well as subjective user input may be included in the input to the front end software. The sensor data may be filtered, and features in the time domain and in the frequency domain may be extracted in order to determine amplitude, range, derivatives, periodicity, and other signal characteristics. The features may be used to automatically classify the information 28 shown on the top right of FIG. 4. Information that may be elicited from the user by use of electronic questionnaires is indicated at 30. Both types of information may be aggregated in local or remote storage device 32. The aggregated information could be used by a treatment expert software unit 34 for automated controls of treatment based on this data. In one embodiment, however, this information may be used for diagnosis and to evaluate treatment response. The clinician may remotely obtain aggregated data from the system as well as remotely deliver instructions concerning treatment to the system. To this end, data exchange with the clinician may be performed.

The front end software may produce a first type of output in the form of summarizing statistics and trends concerning the aggregated information related to the quality of sleep. These outputs may be displayed to the patient. Regression analysis may be used to determine objectively which of the subject's habits have the greatest impact on subjective sleep quality. More generally, regression analysis may be performed based indirectly on any or all of the sensor readings in order to rank the effects of various condition parameters on the length, efficiency and/or lack of movement associated with the patient's sleep. That is, regression analysis may be performed not on the sensor readings directly, but rather on the automatically determined objective measures and the subjective measures. Thus, the relationship between objective measures and subjective patient feedback may be better characterized.

The clinician may use the results of the regression analysis to tailor the intervention for the most efficacious treatment of an individual patient. As this type of information may have an influence on the patient's therapy, the clinician may be able to decide whether the information will be displayed to the patient. The front end software may also produce a second type of output in the form of control of peripherals to give audible, visual, or tactile feedback to the patient in order to deliver CBT treatment, notify the patient of system errors or user errors, and educate regarding the use of the system.

The clinician can access aggregated data as well as raw data for each individual night. Rating of severity of the sleep disorder may follow the procedure of the PSQI. In order to customize DPU 24 to different questionnaires, different or additional questions may be asked. In this case, a modified severity rating scale may need to be provided.

C. System Outline

Previous sections hereinabove have delineated the use of sensors and software and the impact of the system on the therapy regimen of insomnia. This section focuses more on the clinician's perspective of the system and on providing a more comprehensive overview of the use cases. Front end 12 of system 10 is the end most closely coupled to interaction with the patient. Middle end 14 may include a remote database 36 which may store the personal health records of patients and data related to diagnosis and treatment of the patients' sleep disorders.

Clinicians may interact with back end 16, which may include a back end data analysis and diagnosis unit (DADU) 38 with integrated camera and microphone, as indicated at 40, as well as a display screen and keyboard. DADU 38 may run three software modules referred to as "signal processing engine 2", "data analysis visualization", and "diagnosis task management and scheduling".

As shown in FIG. 1, there may be two software modules for signal processing. The software module "signal processing engine 1" may be located in front end 12, whereas module "signal processing engine 2" may be located in back end 16. Thus, signal processing may take place at both front end 12 and back end 16. This can be useful if, due to financial or efficiency considerations, processing capabilities of front end 12 are too limited to classify all attributes of a patient's sleep quality automatically. In this case, sensor data can be transferred to back end 16 where final signal processing takes place. However, in at least one embodiment, sensor data is processed and classified directly on front end 12. The signal processing modules may also be implemented in an embedded microprocessor solution.

The responsibility of the "data analysis and visualization" module in DADU 38 may be to give the clinician a quick overview of a patient's sleep quality. On the display screen, the clinician may observe the patient as well as processed data collected by the environmental and body-worn sensors. Based on the observed data, the clinician may adapt treatment or intervene. One possible way to intervene is to schedule or instantaneously initiate a remote consultation in which the patient can see and/or hear his clinician by virtue of the video camera and the microphone 40 provided in DADU 38. Another possibility for intervention is sending textual reminders to a patient. To this end, DADU 38 may include a keyboard for the clinician to input textual data that may be transmitted to and displayed for the patient. Intervention may be supported by the "diagnosis task management and scheduling" module in DADU 38. Possible embodiments for DADU 38 include smart devices and appliances such as a smartphone or television.

The keyboard in DADU 38 may also be used by the clinician to produce a "tactile signal" that is transmitted to front end 12 and that controls the operation of a tactile actuator, such as a vibrating device worn by the patient. Thus, the clinician can use the tactile actuator to awaken the patient at desired times, such as to keep him on a certain sleeping schedule, or to prompt him to get up out of bed if he has not been able to fall asleep within a desired length of time. It is to be understood that in this context of controlling the tactile actuator, the keyboard may be, in a simple form, merely a pushbutton for sending an activating signal to the tactile actuator.

Notwithstanding the above description, in at least one embodiment, the tactile actuator is used only to wake up a patient when it is scheduled according to his therapy protocol. Further, the system may automatically engage the tactile actuator in order to prompt the patient to get out of bed. The thresholds to engage the tactile actuator may be set by the clinician, however.

Clinicians can also use back end 16 to assess and monitor a patient's sleep quality periodically. Required clinician time during diagnosis and treatment may be reduced even more when front end 12 is employed with automatic diagnosis and treatment capabilities described hereinabove. Even though DADU 38 may be specialized to carry out the above-described tasks, it is also possible within the scope of the invention for a general purpose computer to be used for this purpose instead.

Communication between front end 12, middle end 14, and back end 16 may take place in WAN 26. This may reduce the dependence on the local availability of sleep specialists, and it may increase the number of patients that these clinicians can potentially reach. For remote consultation of clinicians, direct streaming (or peer-to-peer) communication between front end 12 and back end 16 may be called for. For the assessment of data related to sleep quality, both front end 12 and middle end 14 may have sufficient local space to enable store-and-forward communication between front end 12 and back end 16. The use of open security standards readily available in the public domain may ensure privacy and data security. A patient may not be able to access data of other patients in this database, and a clinician may be able to access data of only the patients that the clinician is treating. The database may be managed by a tele-medical center or by another third party.

Electronic system 10 may measure, collect, and aggregate standard attributes of sleep quality used in clinical settings. The data collected may be used to diagnose sleep disorders more accurately than is possible in the prior art. Symptoms of insomnia may be treated using remote cognitive behavior treatment.

System 10 includes features that may be structured into three categories: diagnosis aid features, treatment aid features, and general features. Included in diagnosis aid features, system 10 may provide an instrument for clinicians to remotely diagnose the following disorders: insomnia (primary); sleep breathing disorders, such as central or obstructive apnea based on monitoring patients' nightly activity combined with respiratory events; circadian rhythm disorder based on continuous monitoring of body temperature and human activity levels; periodic limb movement disorder and restless legs syndrome based on identification of motion using body-worn sensors; depression and other health issues by means of additional self-report questionnaires; and altitude insomnia using barometric pressure sensors.

Also included in diagnosis aid features, system 10 may provide assessment of sleep hygiene based on automatic classification of sensors data and user input. Another diagnosis aid feature is that system 10 may provide, in some embodiments, automated diagnosis by virtue of software modules comprising a sleep expert system. Yet another diagnosis aid feature is that system 10 may provide report generation from subjective patient information and automatic classification of quantitative attributes relevant to sleep quality.

Included in treatment aid features, system 10 may provide continuous assessment of treatment response, which may enable clinicians to tailor the type, emphasis, and sequence of treatment components to individual needs. Another type of treatment aid feature is that system 10 may provide uniform evaluation of treatment response and outcome due to use of the same sensors and measurements during both diagnosis and treatment procedures.

Yet another type of treatment aid feature is that system 10 may provide remote delivery of CBT from clinician to patient employing standardized content stored in front end 12, middle end 14 or back end 16. Standardized content may include audio or video recordings. Feedback to the patient for interactive content may be given in the form of audible, visual, textual, or tactile stimulation or a combination thereof. An example is sleep restriction wherein the patient is woken up at a defined time according to therapy protocol. Another example is stimulus control wherein vibrations of body-worn sensors prompt the patient to get out of bed if the patient is unable to fall asleep within thirty minutes.

Still another type of treatment aid feature is that system 10 may provide real-time audio and/or video communications between the clinician and the patient. Such electronic communications may enable the clinician to deliver additional therapy content, interview or examine the patient remotely, or intervene should the outcome of the therapy or the health of the patient be at risk.

A further type of treatment aid feature is that system 10 may provide a "monitoring only" treatment option to reduce the required clinician time. A still further type of treatment aid feature is that system 10 may provide long-term monitoring of patients after a treatment regimen has been completed in order to prevent symptom relapse. Another type of treatment aid feature is that system 10 may provide, in some embodiments, automated treatment through software modules including sleep expert knowledge, as may be embodied by treatment expert 34.

Included in the general features of system 10 are its location; its sensors; its software; the communication between clinician and patient that is enabled by system 10; and the data transmission associated with system 10. By virtue of the location feature, system 10 enables home diagnosis and home treatment.

Advantageously, the body-worn sensors of system 10 are small and do not inconvenience the user. The body-worn sensors may include built-in MEMS inertial sensors and temperature sensors to identify limb movements, and to determine sleep stages, circadian rhythm, and body temperature. One of the body-worn sensors may measure oral and nasal airflow and identify irregular breathing patterns. Passive infra-red motion sensors may identify the patient's presence, motion, and sleep stages.

Advantageously, the sensors of system 10 may work in combination or conjunctively to determine the values of sleep parameters. For example, the combination of body-worn and PIR sensors enables an accurate determination of sleep quality attributes including the patient's bed time; the lengths of time the patient was awake in bed; the time of sleep-onset; the time at which the patient got up; the lengths of time the patient was asleep; the times at which the patient woke up during the night; the times at which the patient got up out of bed during the night; the patient's breathing pattern (e.g., to determine whether or not the breathing is irregular); the degree to which the patient coughs and snores; the degree to which the patient experiences leg twitching and jerking; the degree to which the patient makes other restless movements; and the patient's body temperature. A combination of sensors may also be used to measure the environmental factors of light, noise, vibration, $CO_2$, ambient temperature, humidity, and barometric pressure.

The software of system 10 may include a classification algorithm using time-series and/or statistical modeling approaches to automatically quantify attributes of sleep quality with ground truth (e.g., information that is collected "on location") based on data from polysomnography. The aforementioned signal features may be analyzed using a classifier such as a support vector machine. The outputs of the classifier may be further integrated into temporal models such as a Hidden Markov Model (HMM). An intermediate result of the calculations performed by such models may be an accurate estimation of the activity in which the patient is engaging at a particular point in time (e.g. going to bed, sleeping, tossing and turning, waking up, getting up, raising, etc.) or the various sleep states. A sequence of activity classifications may be used to rate/quantify most sleep quality attributes. One advantage of the system of the invention is that the patient may not have to wear EEG sensors during the night in order for the system to distinguish sleep from wake phases. The software may employ a distributed architecture of signal processing algorithms that makes it possible to divide the tasks of automatic quantification of sleep quality attributes between front end 12, the middle end 14, and back end 16. The software may enable automatic determination of quantitative information asked on clinical questionnaires such as the PSQI on a nightly basis. The software may make use of electronic questionnaires based on the clinical questionnaire PSQI to inquire about subjective information from a patient regarding sleep quality. The software may provide audible and/or visual feedback to correct user errors. For example, a video can show how to use a body-worn sensor should the user forget to activate or mount the sensor correctly.

The communication between the clinician and the patient that may be enabled by the software of system 10 which may include remote audio and video consultations in which the clinician can interview patients or intervene in diagnosis or treatment procedures. The patient and the clinician may be able to view the real-time sensor data at the same time.

The software of system 10 may enable front end 12 to receive multiple video streams, and back end 16 may be enabled to switch between video streams transmitted to front end 12. Thus, the clinician may be able to show standardized instructional videos to the patient in order to instruct the patient about how a measurement needs to be taken, for example.

The software of system 10 may enable front end 12 and back end 16 to facilitate scheduling of appointments between the patient and the clinician for remote consultations. Thus, both the patient and the clinician may be able to send appointment requests to each other. Further, either the patient or the clinician may be able to accept, decline, or suggest alternative times as a response to an appointment request.

In one embodiment, sleep quality of patients may be determined on a nightly basis by the front end 12. This information may be forwarded to the middle end 14 where it may be stored in a local or remote database, from where sleep specialists can retrieve it for review at a later time. Sleep specialists review the information stored in the data base by means of back end 16. In cases in which patients need to be monitored more closely, sleep specialists may observe sensor data, automatically determined sleep quality attribute ratings, and a video transmission of the sleeping patient in real-time. To this end, the data transmission associated with system 10 may include data transmission for remote consultation that is done in real-time using point-to-point communication between front end 12 and back end 16. In addition, data related to patients' sleep quality may be transmitted from front end 12 to middle end 14 or to back end 16 in real-time, or the data may be stored in front end 12 and forwarded at a later time. Data may be buffered for extended periods of time by front end 12, and can therefore be collected by back end 16 at a later point in time.

In one embodiment, the invention includes a method of quantifying a patient's sleep quality and treating a patient with a sleep disorder. At least one environmental condition is sensed within an environment in which the patient engages in sleep activity. A condition of the patient during the sleep activity is sensed. Information about the sensed environmental condition and the sensed condition of the patient is transmitted to middle end 14 where it is stored in the remote data base 36. The information stored in this data base consists of values for the aforementioned sleep quality attributes derived from the sensor data acquired at the patient's premises by means of the front end 12. A tactile actuator, preferably integrated into the body worn sensors 22, is worn by the patient during the sleep activity. Patients receive treatment before they go to bed and while they are in bed. More precisely, the before mentioned CBT components stimulus control and sleep restriction therapy are facilitated by the tactile actuator while a patient is in bed. Thus, this part of the treatment is administered automatically by the display and processing unit 24 which controls the tactile actuator in the body worn sensor 22 located on the patient's body. The other components of CBT, such as relaxation therapy, cognitive therapy, and education on sleep hygiene are delivered during the day or before the patient goes to bed in order to try to initiate sleep.

In an example treatment module "sleep restriction," which may be part of the therapy, the "maximum amount of time the patient is allowed to spend in bed" may be a critical parameter for the part of the therapy concerned with sleep restriction. Initially, this parameter may be restricted to a fixed value, for example four hours. Typically, this parameter may be increased only if the patient's sleep efficiency (e.g., time in bed/time asleep) is greater than 85%. The system may automatically measure "time in bed" and "time asleep" along with other attributes of sleep quality. The combination of all attributes of sleep quality may enable the sleep specialist to determine whether or not to increase the treatment parameter "maximum amount of time the patient is allowed to spend in bed". Consequently, when this parameter is increased, the front-end may prompt the patient to go to bed at an earlier time or it may wake the patient up later in the morning.

The invention may provide several novel features which are described in more detail below. Such novel features include:

1. Automated classification of attributes characterizing sleep quality by the front end. This classification may be enabled by the unique set of sensors.
2. Set of attributes rated by the patient manually/subjectively.
3. The ability to perform regression analysis on both automatically rated attributes and manually/subjectively rated attributes.
4. Trending of treatment progress during or at the end of every phase of the (CBT) therapy.
5. Enabling technology for clinicians to review current and past sleep quality of their patients offline, draw conclusions from the observed patient's progress, and modify the protocol accordingly without having to monitor patients in their sleep in real-time.

1. Automated Classification of Attributes Characterizing Sleep Quality

Figure 6:
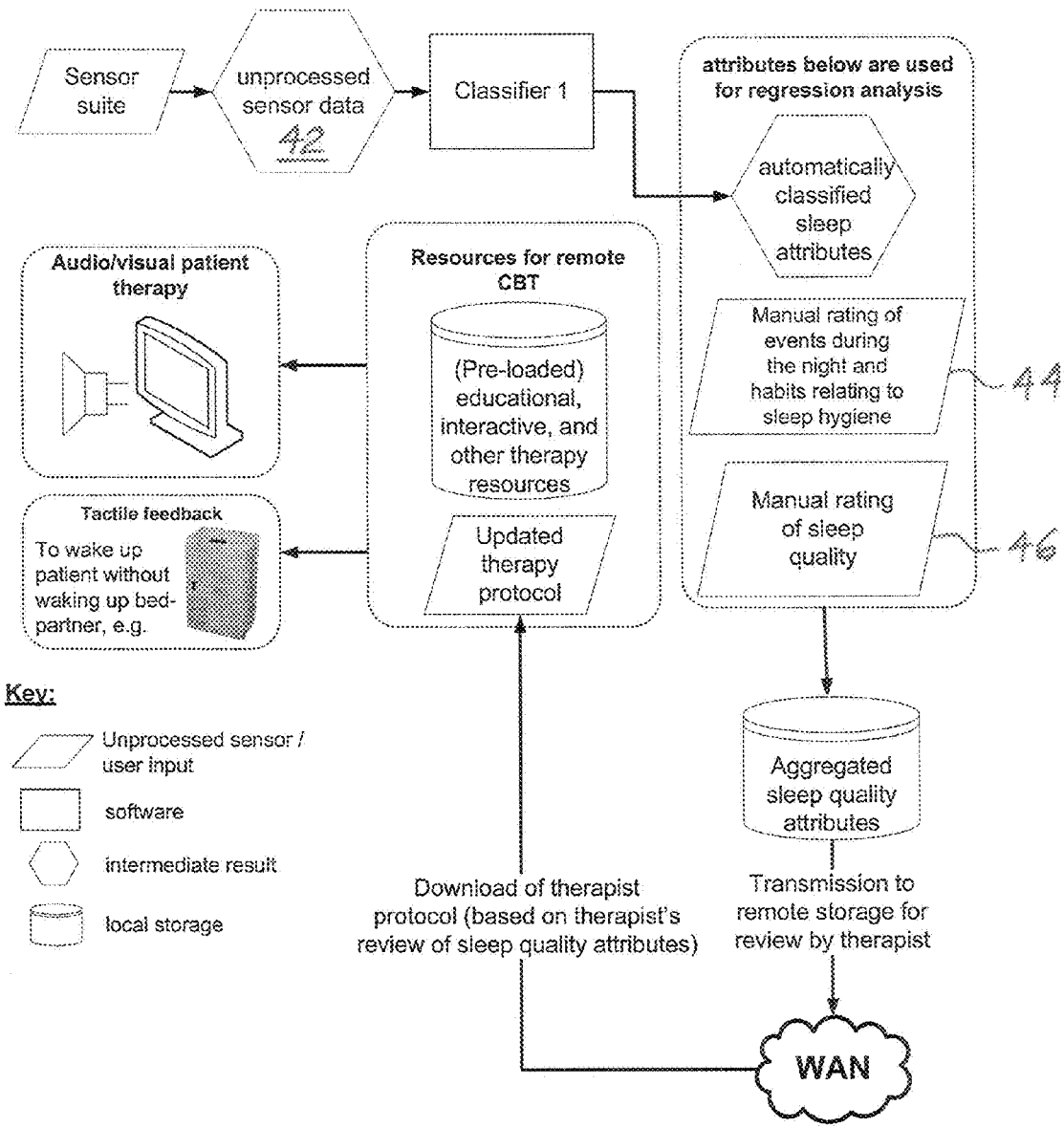
FIG. 6 is a data flow diagram of one embodiment of the front end of the system of FIG. 1.

The data flow diagram of FIG. 6 provides a high-level overview of parts of front end 12. Audio/video communication features which enable front end 12 to communicate with a clinician using back end 16 of system 10 are not depicted in FIG. 6 for the sake of brevity.

As depicted in FIG. 6, the input to front end 12 may include raw/unprocessed sensor data 42, manual/subjective user input 44 relating to events during the night and habits possibly affecting sleep hygiene, and manual/subjective user input 46 relating to the perceived sleep quality of the patient.

"Classifier 1" is a part of the software that runs on front end 12 to provide accurate ratings of sleep quality attributes. This software may use the sensor data as an input, and Classifier 1 may process the sensor data in real-time. Thus, for every point in time the system may have an (accurate) rating of most sleep quality attributes. The system may not provide these automatic ratings for all sleep attributes, however. Some of the attributes may be impossible or at least inherently difficult to rate automatically. The type of medication taken at some time during the day may be one such attribute, for example. The information that cannot be classified automatically may be entered by the user manually. The table shown in FIG. 7 provides an overview of the attributes that may be classified automatically and those that may be entered manually by the patient.

The sensor data may be filtered, and signal features in the time domain and in the frequency domain may be extracted in order to determine amplitude, range, derivatives, periodicity, and other signal characteristics. Examples of relevant signal characteristics (i.e., features) from the body-worn three-dimensional inertial sensors include, but are not limited to, sensor orientation (with respect to the gravitational force), energy expenditure, and spectral flatness. Some of these features may be calculated based on a sequence of a fixed number of consecutive sensor readings.

The Classifier 1 software may employ biomechanical and/or statistical models. These models analyze signal features mentioned previously to arrive at the classification result. One advantage of the proposed system is that the patient does not have to wear EEG sensors during the night in order for the system to distinguish sleep from wake phases.

An intermediate result of the calculations performed by Classifier 1 may be an (accurate) estimation of the activity in which the patient is engaging at a particular point in time (e.g., going to bed, sleeping, tossing and turning, waking up, getting up, raising, etc.). A sequence of activity classifications may be used to rate/quantify most sleep quality attributes.

The automatic ratings may be augmented with the patient's manual/subjective feedback relating to events that happened during the night and certain habits that the patient followed before going to bed. In addition, patients may provide a manual/subjective rating of their perceived overall sleep quality after rising in the morning.

All manual/subjective feedback and all automated classifications may be aggregated on a per night basis to a sleep report. Sleep reports may be uploaded to a remote database where a clinician (specializing in sleep medicine) can review the data that is contained in the reports. Minimal effort may be needed by the clinician to review the data in order to assess the progress of each individual based on the currently delivered part of the multi-stage CBT therapy. Clinicians may be able to easily determine based on the reviewed reports which therapy parts delivered so far have had the most beneficial impact on the patient. This information may be used to individualize the treatment to possibly achieve better treatment outcomes. The information may also be used to prevent symptom relapse more effectively by providing an individualized recap which emphasizes those parts of the treatment that have been shown to be most effective for the particular patient.

In using the inventive system, treatment does not need to be delivered by the clinician manually, but rather CBT therapy may be delivered remotely. One part of remote delivery of CBT can include educational videos and text that can be reviewed interactively using electronic questionnaires or games. While the system of the invention can certainly offer (pre-loaded) audio/visual and textual education material, the system can also assist with various other parts of CBT treatment that traditionally require the feedback of a clinician. An example of this can be seen in the stimulus control part of CBT. During stimulus control therapy, patients may be instructed to get out of bed if they cannot fall asleep. After getting out of bed, the patients are further instructed to engage in a relaxing activity until they feel tired again. It may be counterproductive for insomnia patients to frequently check the clock as they are trying to fall asleep. The system of the invention may use tactile feedback to prompt the patient to leave the bed if the patient has not been able to initiate sleep within a predetermined length of time. Likewise, the system of the invention can assist with the sleep restriction part of CBT. Sleep restriction therapy may allocate a fixed time window every night in which the patient is instructed to try to sleep. Patients are instructed not to try to initiate sleep earlier, and they are instructed not to rise later than prescribed. The system of the invention may not only track when a patient is not in compliance with the instructions, but it may also correct the patient using tactile, audible, or visual feedback. As far as the relaxation therapy part of CBT is concerned, the inventive system may monitor by means of the body-worn sensors whether or not the patient is engaging in the prescribed light physical exercises. In addition, the inventive system may also determine whether or not the patient is doing the exercises correctly.

2. Set of Attributes Rated by the Patient Manually/Subjectively

Figure 8:
FIG. 8 is a diagram of one embodiment of a user interface of a data and processing unit of the front end of the system of FIG. 1. A patient may interact with this user interface before trying to initiate sleep.

Before going to bed, patients may be instructed to indicate the type of daytime activity during which they had trouble staying awake. Possible answers from the patient may include "none", "driving", "eating meals", "social activity", and "watching TV". The patient may also be asked to what degree the patient felt motivated to get things done. Possible answers may include "no problem", "slight problem", "somewhat of a problem", or "big problem". Finally, in order to rate sleep hygiene more comprehensively, the patient may be asked to answer whether or not he consumed food, alcoholic or caffeinated beverages, sleeping aids, or engaged in mentally or physically stimulating activity shortly before bed time. Each of these questions may be answered within just a few seconds due to the use of a touch screen or pushbuttons on the DPU. An embodiment of a DPU that is equipped with automatic speech recognition may enable even more efficient user interaction. The patient may provide this information in a matter of seconds by using a touch-screen displaying a user interface such as user interface 48 (FIG. 8).

In the example user interface 48, a patient has selected to have had a meal, an alcoholic beverage, and stimulating mental activity two hours or less before going to bed. The patient has furthermore indicated to have taken no medication today, and he also denies having had any trouble staying awake during standard daytime activities.

Figure 9:
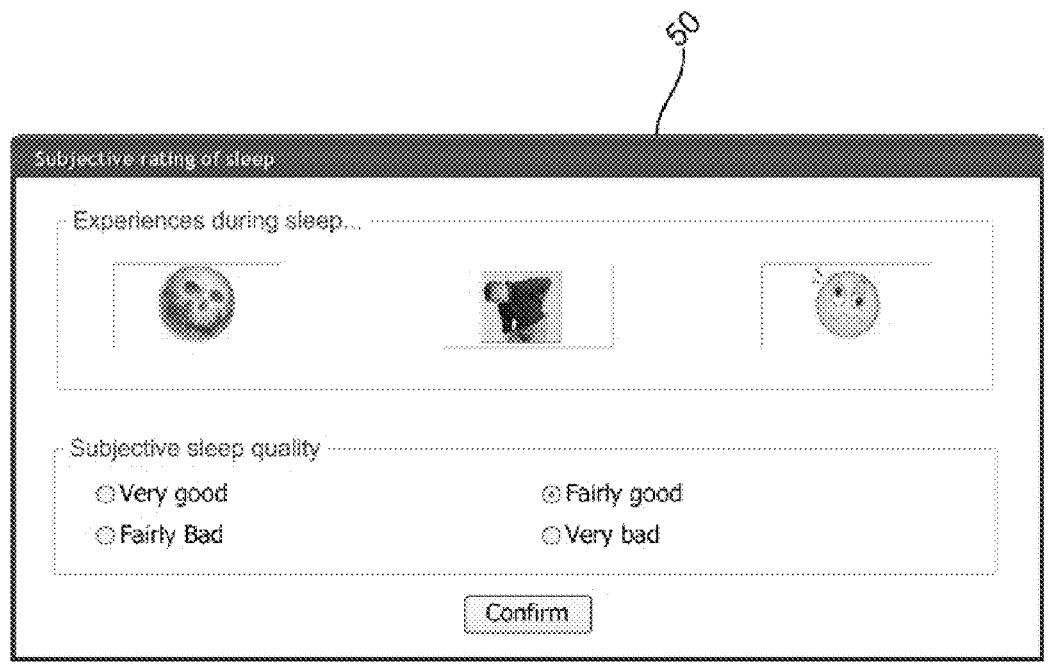
FIG. 9 is a diagram of an embodiment of a user interface of a data and processing unit of the front end of the system of FIG. 1. A patient may interact with this user interface after rising in the morning.

After the patient rises in the morning he may be prompted to provide additional information on a user interface similar to user interface 50 in FIG. 9. The patient may use DPU 24 to manually enter whether or not he had disturbing dreams, felt disoriented or confused while asleep, or was in pain. The patient may also rate his sleep quality subjectively. Possible ratings may include "very good", "fairly good", "fairly bad", or "very bad". In the example user interface 50, the patient has selected to have experienced nightmares and disorientation during the night, yet the patient has rated his sleep quality as "fairly good".

The subjective feedback from the patient before going to bed and after awakening, as well as the quantitative information determined automatically by DPU 24 may provide not only the information elicited by the PSQI, but also more details regarding the sleep hygiene of the patient. The information may be aggregated such that a clinician may obtain a quick overview regarding the number of times the patient, for example: could not fall asleep within thirty minutes; woke up in the middle of the night or early in the morning; got up in the middle of the night (e.g., to use the bathroom); could not breathe comfortably; coughed or snored loudly; was too hot, or too cold; had disturbing dreams; was in pain; or had generally poor sleep hygiene.

3. Ability to Perform Regression Analysis on Both Automatically Rated Attributes and Manually/Subjectively Rated Attributes Ratings of the sleep quality attributes listed in FIG. 7 may quantify the duration and continuity of sleep. The ratings furthermore may indicate factors contributing to sleep quality such as the extent to which a subject exposes himself to environments that are not conducive to sleep and how frequently a subject follows habits that are known to negatively affect duration, continuity, and restorative functions of sleep. In addition to that, the inventive system may take into account the subjective perception of overall sleep quality.

The data provided by the inventive system may be used in a number of ways to optimize sleep. Traditionally, CBT treatment aims at maximizing sleep efficiency. Sleep efficiency may be defined as the ratio of the length of time asleep to the length of time spent in bed. Regression analysis may be used to determine which other attributes influence sleep efficiency the most. Likewise, regression analysis may focus on identifying the attributes that have the biggest impact on subjectively perceived overall sleep quality. In one embodiment of the inventive system, this information may be shown to the clinician who may adapt the therapy protocol accordingly. In another embodiment this information may be displayed to patients to motivate them to change their behavior. In yet another embodiment, the system may perform this analysis automatically and use this information to automatically adapt treatment in order to maximize treatment outcome.

Figure 10:
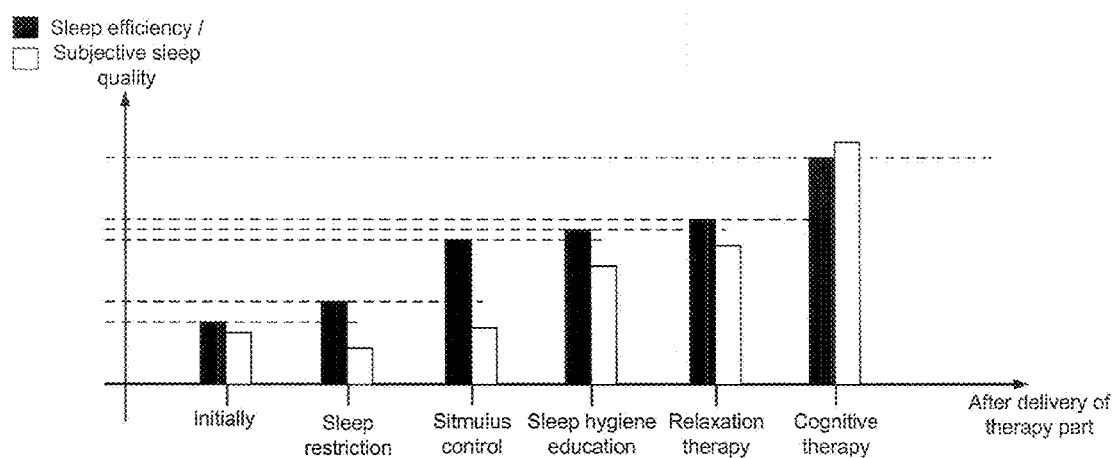
FIG. 10 is an example bar chart of the attributes "subjective overall sleep quality" and "sleep efficiency" across sequential phases of CBT treatment.

4. Trending of Treatment Progress During or at the End of Every Phase of the (CBT) Therapy Apart from the regression analysis mentioned in Section 3 above, simple trending may be used as a powerful tool in helping clinicians and patients identify the part of therapy from which they have benefitted the most with regards to a certain quality attribute. This insight may be used in follow-up booster sessions to prevent relapses by focusing stronger on a patient's individual need. FIG. 10 shows a hypothetical example of the development of sleep quality over the course of CBT treatment. More specifically, FIG. 10 illustrates how the attributes "subjective overall sleep quality" (shown in white bars) and "sleep efficiency" (shown in black bars) may be used to follow the progress during each phase of the therapy.

5. Enabling Technology for Clinicians to Assess a Patient's Sleep Quality Without Having to Watch the Patient Remotely By use of the invention, the clinician may not need to watch patients while they are asleep in order to assess their sleep quality. Assessment of sleep quality may be done as described in Section 1 above. In a small number of cases, however, it may be useful for the clinician to assess certain irregular night time activity by means of real-time video originating from the front end. In this case, it might be helpful for the clinician to have a means to awaken the patient, for example by using tactile feedback in order to prevent harm to the patient or to others.

System 10 may provide quantification of a set of factors impacting quality of sleep, such as the maximum sleep duration, counterproductive body movement (e.g., restlessness), etc. in real-time. A review of a particular patient's sleep history with regards to the above factors may be provided. System 10 may provide an assessment of sleep quality based on the above data.

As applied to geriatric patient care, system 10 may detect and/or predict uncomfortable sleep, and predict whether a patient will try to get out of bed. Data from body-worn sensors may be used to predict or detect a patient falling out of bed. For example, a sensor may detect an unusual breathing pattern that may precede and/or coincide with a patient falling out of bed. System 10 may automatically alert the staff of a health care facility in the event that system 10 detects and/or predicts a patient getting out of bed or falling out of bed. In one embodiment, the sensed conditions of the patient may be used to predict a likelihood that the patient will get out of bed or fall out of bed within a predetermined time period. The predetermined time period may be within the next ten minutes, for example. If the likelihood exceeds a threshold level (e.g., exceeds a threshold level of approximately between one and five percent), personnel disposed at the health care facility may be automatically informed of the likelihood being above the threshold level. For example, an alarm may sound in the patient's room, a text message may be transmitted to personal communication devices carried by the personnel, and/or a warning message may be sent to a central, monitored computer at the health care facility.

For all types of patients, system 10 may provide detection and/or prevention of sleep disorders. Further, system 10 may predict and/or detect the occurrence of sleep apnea, nightmares, sleepwalking, etc. After having predicted and/or detected these conditions, system 10 may record the occurrence and/or alert the patient or medical staff Another possible application of system 10 may be in the area of fitness and wellness. System 10 may be used by adults trying to improve their quality of rest, or who are striving to correct the problem of a lack of rejuvenating sleep. System 10 may assess disturbing factors which may impact sleep, review sleep history, and enable the user to draw self-conclusions about possible problems or issues negatively affecting their sleep quality.

Wherein a video display has been disclosed herein, it is to be understood that the video display may include a speaker for producing audio sounds in correspondence with the video images shown on the display. It is to be further understood that the processing apparatus that produces the video signal shown on the display may also produce an audio signal that is played on the speaker. Such video and audio signal may be dependent upon output signals from the associated camera and microphone, respectively.

Figure 5:
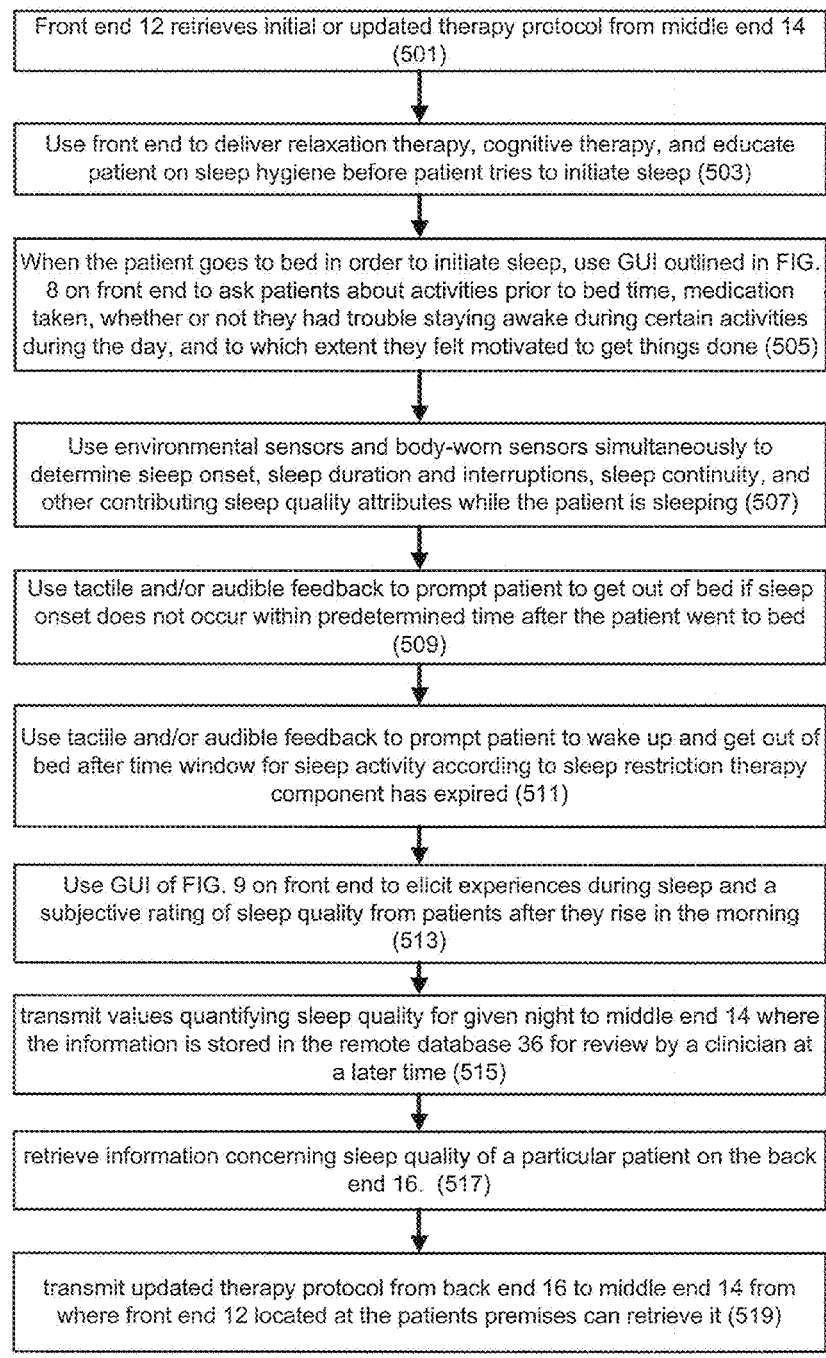
FIG. 5 is a flow chart of one embodiment of a method of the present invention for treating a patient who has a sleep disorder.

In FIG. 5, there is shown one embodiment of a method 500 of the present invention for treating a person who has a sleep disorder. In a first step 501, the front end 12 may automatically retrieve the initial therapy protocol from the middle end 14, e.g. right after the front end has been set up on the patients premises or when the patients starts interacting with the DPU 24 in order to receive cognitive behavioral therapy. At later points in time, the DPU 24 of front end 12 may automatically look for updates of the therapy protocol on the remote middle end 14.

Next, in step 503, the front end may deliver relaxation therapy, cognitive therapy, and educate a patient on sleep hygiene. It may also remind the patient of upcoming prescribed bed time according to the current protocol for sleep restriction and stimulus control therapy.

Next, in step 505, the graphic user interface (GUI) shown in FIG. 8 may be used shortly before the patient goes to bed in order to initiate sleep. In particular, the patient may be asked in what type of activities they engaged in the last 2 h prior to their bed time, during which daytime activities they had trouble staying awake, what types of medication they have taken during the day, and to which extent they felt motivated to get things done.

In step 507, at least one environmental condition within an environment in which the patient engages in sleep activity may be sensed. That is, various environmental sensors may be provided within a room in which the patient sleeps or at least attempts to sleep. The environmental sensors may measure different parameters that may affect the comfort of the patient, and thus may affect his ability to sleep. Examples of such environmental sensors include carbon dioxide sensors, thermometers, light sensors, humidity sensors, barometric pressure sensors, noise sensors, and vibration sensors. The environmental sensors may also include motion detectors for sensing movement within the room of people (e.g., bed partners and pets), fans, or wind-blown items, or even of the patient himself. At the same time, a condition of the patient during the sleep activity may be sensed. For example, various sensors may be worn on the patient's body or may be placed in association with the patient's body for determining the state of the patient's bodily functions while he is sleeping or at least attempting to sleep. Such body-worn sensors may include air-flow sensors, inertial sensors for measuring the type and intensity of the patient's movements, and thermometers. It may be also possible for a sensor to detect a condition of the patient during the sleep activity without the sensor touching or physically engaging the patient. For example, a thermal infrared imager may determine temperatures at various locations in and/or on the patient's body without touching the patient.

In step 509, tactile and/or audible feedback may be used, if needed, in order to prompt a patient to get out of bed if sleep onset does not occur within predetermined time after the patient went to bed. This length of this time duration may be determined by the clinician responsible for the therapy of the patient.

Thereafter, in step 511, when the prescribed rising time has been reached in the morning, tactile and/or audible feedback may be used to wake up the patient in the morning and prompt him or her to get out of bed. The prescribed rising time may be determined remotely by the clinician after reviewing the information pertaining to a patient's past sleep quality.

In step 513, the GUI shown in FIG. 9 may be used to elicit form the patient whether he or she experienced pain, had nightmares, or felt disoriented during the night. The patient may be asked furthermore, how they personally would rate the quality of their sleep from the night before.

Next, in step 515, information about the sensed environmental condition and the sensed condition of the patient is transmitted to the middle end 14 at a remote location. For example, data processing unit 24 may collect sensor readings from each of the above-described sensors and transmit information related to the sensor readings to the remote database 36 disposed at the middle end 14. The sensor readings may be aggregated and/or reports may be generated based thereon, and such may be the basis for the transmitted information. The information may be transmitted via telephone lines, the internet, or other WANs 26 for example.

In step 517, a clinician may retrieve information concerning the sleep quality of a particular patient on an embodiment of back end 16. He/she may review this information on the DADU 38 disposed at his/her location. Reviewing this information may enable a clinician to identify deficiencies of the current therapy protocol. To counter these deficiencies, the clinician may make adjustments to the therapy protocol remotely, e.g. change prescribed times of going to bed and rising, increase or decrease length of time window for sleep activity according to sleep restriction therapy component, or prescribe different type of relaxation exercises, etc.

In step 519, the clinician may transmit the updates to the therapy protocol from the DADU 36 of the back end 16, located at the clinician's premises, to the middle end 14, which may be at a remote location, from where the DPU 24 of front end 12, located at the patient's premises, may retrieve it. The retrieval of the updated therapy protocol may take place as described above.

Steps 508, 510, and 512 may apply if a patient needs to be monitored closely, for example because he poses a risk to himself or to others due to sleep-walking or other irregular night time activities. In step 508, two-way electronic video and audio communication between the patient and the remote clinician may be enabled such that the clinician can see and hear the patient during the sleep activity. For example, a camera, microphone, audio speaker and video display screen may be provided at both the location where the patient sleeps and at a remote location where the clinician works. Similar to video telephones, the outputs of the camera and microphone in one location may be transmitted and serve as inputs for the speaker and display screen at the other location.

In a next step 510, a tactile actuator may be worn by the patient during the sleep activity. For example, a vibrating device may be worn anywhere on the patient's body during the sleep activity. In other embodiments, the vibrating device may be attached to the patient's bed such that the device's vibration may serve to wake up the patient or at least get his attention.

In a final step 512, the patient may be treated after the transmitting step has begun. The treatment may be administered from the remote location via the video communication, the audio communication, and/or the tactile actuator. For example, after the information related to the sensor data has been transmitted to the clinician and he has determined a best course of treatment, the clinician may provide cognitive behavior therapy to the patient by communicating with the patient via the patient's video screen and/or speaker. The treatment may pertain to any time period, such as that particular night's sleep or what the patient should do in the next few minutes, for example. The treatment may also be in the form of tactile stimulation delivered via the vibration device, which may be controlled remotely by the clinician via the telephone lines, the internet (e.g., WAN 26), or radio frequency signals, for example. The patient may already be aware of what he should do after feeling the vibration (e.g., get out of bed), or the vibration may serve to awaken the patient at a time chosen by the clinician.

Figure 11:
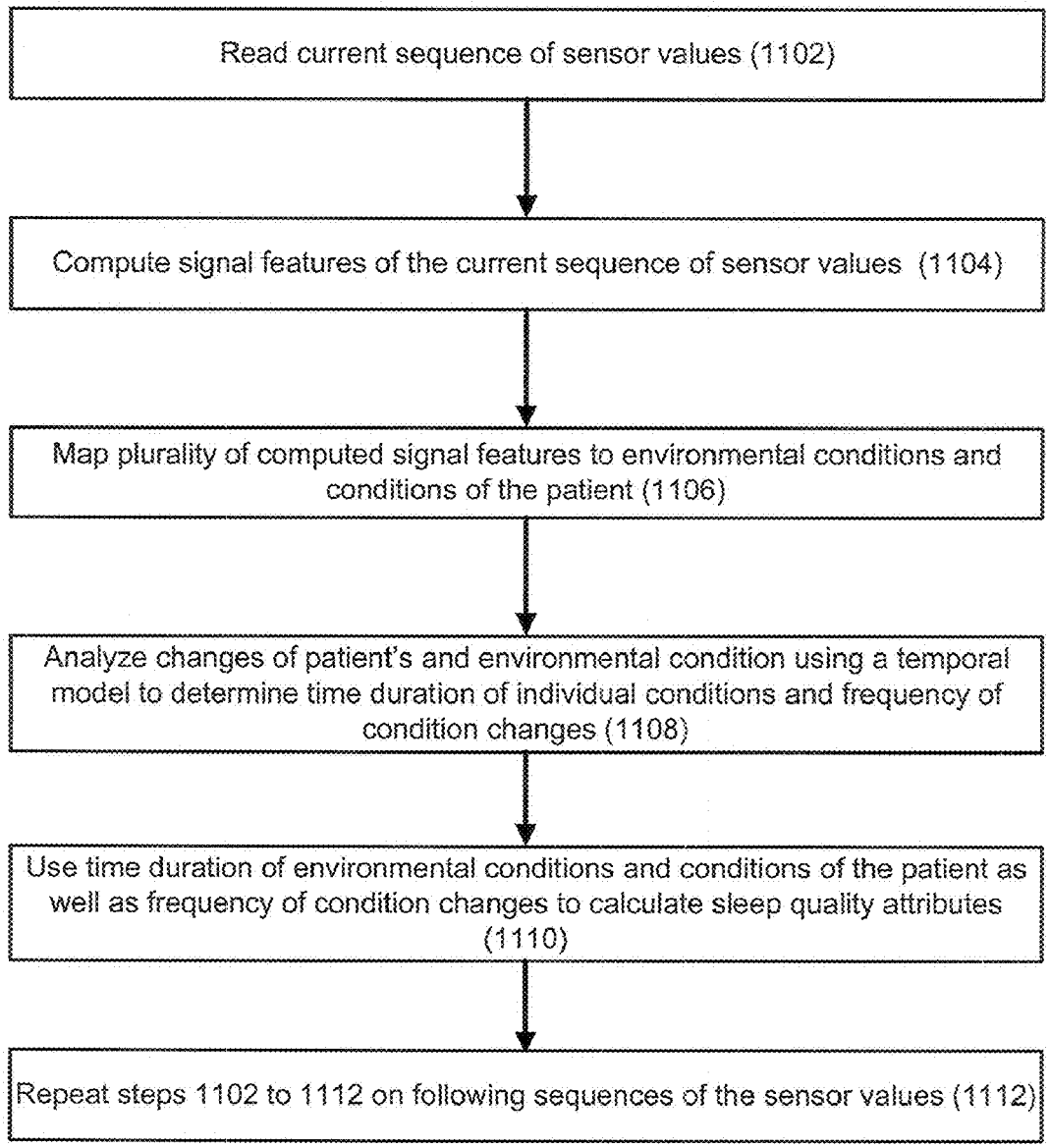
FIG. 11 is a flow chart of one embodiment of a method of the present invention for determining sleep quality attributes based on environmental conditions and conditions of the patient.

The steps that are performed by the display and processing unit 24 to automatically classify environmental conditions and the conditions of the patient are depicted in the flow chart of FIG. 11. In an initial step 1102, a current sequence of sensor values from the environmental sensor and the sensors worn by the patient are read into the random access memory (RAM) of the first processing unit 24. A current sequence of sensor readings is a sequence of values that have been acquired from the sensors mentioned above within a limited time frame, for example within the lasts 30 seconds.

In a next step 1104, one or more signal features are calculated on the sensor data in the RAM of the DPU 24. Examples for these signal features include amplitude, range, derivatives, periodicity, sensor orientation (with respect to the gravitational force), energy expenditure, and spectral flatness.

In a next step 1106, the signal features calculated in step 1104 are used as the input of a predefined mapping which determines an estimate of the current environmental condition and the condition of the patient.

In step 1108, a temporal model, such as a Hidden Markov Model or a Kalman Filter, uses the current and previous estimates of environmental conditions and conditions of the patient in order to determine the most likely sequence of conditions. Steps 1104, 1106, and 1108 are performed by the DPU 24, which keeps track of the duration a particular environmental condition or a condition of the patient persists. DPU 24 also keeps track of the point in time at which a change of the environmental condition or the condition of the patient occurs. In this way, both duration and frequency of change of these conditions can be measured.

In step 1110, duration and frequency of change of the environmental conditions and the conditions of the patient are used to determine the sleep quality attributes listed as information 28 and 30 in FIG. 4.

As the DPU 24 continuously acquires sensor values, in step 1112 a next sequence of sensor readings are used to repeat steps 1102 to 1112.

In further embodiments, verbal feedback may be collected from the patient as to the quality of his sleep and/or what he has been aware of or what has kept him awake. Patients may provide the verbal feedback via a microphone disposed at their premises, or textually via a keyboard disposed at his premises. The feedback provided by a patient may be electronically transmitted to the clinician at the remote location. In one embodiment, the feedback is used within DADU 38 as a factor in the automated diagnosis produced by DADU 38. In addition, or alternatively, the feedback may be audibly and/or textually shared with the clinician so that he may use his judgment in adjusting his recommended treatment based on the feedback provided by the patient.

In other embodiments, the clinician may remotely treat the patient by remotely controlling the tactile actuator to prompt the patient to get out of bed in response to the transmitted information indicating that the patient has been unable to fall asleep after a period of time. For example, the clinician may prompt the patient to get out of bed after a predetermined time period (e.g., thirty minutes) has passed without the patient being able to fall asleep. In another embodiment, the time period is not predetermined, but rather is automatically adjusted based on sensor readings. That is, the patient may be prompted after thirty consecutive minutes of favorable sleeping conditions, as indicated by the sensors, have passed without the patient being able to fall asleep.

In another embodiment, the tactile actuator may not be used directly by the clinician. Rather, the tactile actuator may be used as a means for providing feedback to the patient without disturbing his bed partner.

Although the invention has been described herein as being used to treat human sleep disorders, it may also be used to treat sleep disorders in animals in a non-obtrusive way. Further, the invention may be used to treat other types of disorders, or to diagnose diseases, in humans or animals.

While this invention has been described as having an exemplary design, the present invention may be further modified within the spirit and scope of this disclosure. This application is therefore intended to cover any variations, uses, or adaptations of the invention using its general principles.

What is claimed is:

1. An arrangement for monitoring a patient's sleep activity, comprising:
   at least one environmental sensor configured to sense a condition within an environment for sleeping;
   at least one body-worn sensor configured to be worn by the patient during the sleep activity and configured to sense a condition of the patient during the sleep activity;
   a first communication apparatus including a first camera, first microphone, first audio speaker and a first video display disposed proximate at least one of the sensors;
   a second communication apparatus including a second camera, second microphone, second audio speaker and second video display disposed at a location remote from the first communication apparatus;
   a first processing means communicatively coupled to the environmental sensor, the body-worn sensor, and to the first communication apparatus, the first processing means being for:
      collecting and aggregating sensor readings from the environmental sensor and from the body-worn sensor;
      deriving conditions of the patient and the environment based on the sensor readings;

preparing a report based on the aggregated sensor readings;

receiving output signals from the first microphone and the first camera;

providing a first audio signal played on the second audio speaker and at least partially based on the output signal from the first microphone; and providing a first video signal displayed on the second video display and at least partially based on the output signal from the first camera and on the report;

first means for transmitting the report, the first audio signal and the first video signal to a database at the remote location, the first transmitting means being communicatively coupled to the first processing means, the database being accessible by a clinician; and a second processing means communicatively coupled to the second communication apparatus, the second processing means being for:

receiving output signals from the second microphone and the second camera;

providing a second audio signal played on the first audio speaker and at least partially based on the output signal from the second microphone; and providing a second video signal displayed on the first video display and at least partially based on the output signal from the second camera; and second means for transmitting the second audio signal and the second video signal to the first processing means, the second transmitting means being communicatively coupled to the second processing means.

2. The arrangement of claim 1 wherein the environmental sensor comprises a motion detector configured to sense movement of the patient.

3. The arrangement of claim 1 wherein the body-worn sensor includes at least one inertial sensor.

4. The arrangement of claim 1 wherein the first processing means is for performing regression analysis on automatically determined objective measures, subjective measures, and current therapy progress.

5. The arrangement of claim 1 wherein the first and second transmitting means are communicatively coupled over a packet switching or circuit switching wide area network.

6. The arrangement of claim 1 wherein the second video signal is at least partially based on the report.

7. The arrangement of claim 1 wherein the first processing means is for performing a diagnosis of the patient at least partially based on the report.

8. An arrangement for treating a patient having a sleep disorder, comprising:

at least one environmental sensor configured to sense a condition within an environment for sleeping;

at least one body-worn sensor configured to be worn by the patient during the sleep activity and configured to sense a condition of the patient during the sleep activity;

a tactile actuator configured to be worn by the patient;

a first communication apparatus including a first camera, first microphone, first audio speaker and first video display;

a second communication apparatus including a second camera, second microphone, second audio speaker and second video display is disposed at a location remote from the first communication apparatus;

a first processing means communicatively coupled to the environmental sensor, the body-worn sensor, the tactile actuator, and to the first communication apparatus, the first processing means being for:

collecting sensor readings from the environmental sensor and from the body-worn sensor;

receiving output signals from the first microphone and the first camera;

providing a first audio signal played on the second audio speaker and at least partially based on the output signal from the first microphone;

providing a first video signal displayed on the second video display, the first video signal being at least partially based on each of the output signal from the first camera, the sensor readings, and subjective ratings by the patient; and aggregating the sensor readings and producing a report at least partially based on the aggregated sensor readings;

first means for transmitting the first audio signal, the first video signal and the report to a database at the remote location, the first transmitting means being communicatively coupled to the first processing means, the database being accessible by a clinician; and a second processing means communicatively coupled to the second communication apparatus, the second processing means being for:

receiving output signals from the second microphone and the second camera;

providing a second audio signal played on the first audio speaker and at least partially based on the output signal from the second microphone;

providing a second video signal displayed on the first video display and at least partially based on the output signal from the second camera; and providing a tactile signal controlling the tactile actuator; and second means for transmitting the second audio signal, the second video signal, and the tactile signal to the first processing means, the second transmitting means being communicatively coupled to the second processing means, wherein an image displayed on the second video display is dependent upon the sensor readings.

9. The arrangement of claim 8 wherein the first communication apparatus is disposed within the proximity of at least one of the sensors, such that communication in the ISM band can take place.

10. The arrangement of claim 8 wherein the first transmitting means is for transmitting information related to the sensor readings to the remote location.

11. The arrangement of claim 8 wherein the tactile actuator comprise a vibration-generating device.

12. The arrangement of claim 8 wherein the second communication apparatus is disposed at a location remote form the patient, the second communication apparatus including a keyboard, wherein the second processing means is for:

receiving output signals from the keyboard; and providing the tactile signal dependent upon an output signal from the keyboard.

13. A method of treating a patient who has a sleep disorder, the method comprising:

sensing at least one environmental condition within an environment in which the patient engages in sleep activity;

before the sleep activity, enabling the patient to enter factors that may contribute to the quality of his sleep;

during the sleep activity, sensing a condition of the patient;

after the sleep activity, enabling the patient to manually rate factors that may have contributed to the quality of his sleep;

electronically transmitting information about the sensed environmental condition and the sensed condition of the patient to a clinician at a remote location;

providing a tactile actuator that is worn by the patient during the sleep activity; and treating the patient before and while the patient is trying to initiate sleep or while the patient is already sleeping, the treatment being administered either by the arrangement of claim 8 or from the remote location via at least one means of audio communication and the tactile actuator, the treatment being dependent upon:

the factors entered by the patient before the sleep activity; and the ratings of the factors provided by the patient after the sleep activity.

14. The method of claim 13 wherein the environmental condition includes temperature, humidity, barometric pressure, noise level, light level, carbon dioxide level, or movement within the environment.

15. The method of claim 14 comprising the further steps of:

automatically filling out sleep diaries and clinical questionnaires on behalf of the patient based on data related to the sensor readings of the arrangement of claim 7;

summarizing the information contained in the filled out sleep diaries and questionnaires into a report;

automatically diagnosing the patient at the location of the first or second processing means of claim 1 based upon the data used to automatically fill out sleep diaries and clinical questionnaires;

communicating the automatically filled out sleep diaries and questionnaires, the report, and the diagnosis to the clinician, wherein the treating step occurs after the diagnosis has been communicated to and accepted by the clinician, and wherein the treating step include adjusting frequency and duration of therapy program; and transmitting a request to the patient to prompt consultation with the treating clinician directly or remotely, automatically controlling the tactile actuator to prompt the patient to get out of bed in response to the transmitted information indicating that the patient has been unable to fall asleep after a period of time.

16. The method of claim 13 wherein the condition of the patient includes body temperature, nasal and/or oral air-flow, or a type or intensity of movement by the patient.

17. The method of claim 13 comprising the further steps of:

calculating at least one signal feature of the sensor readings from the environmental and body-worn sensors by virtue of the first processing means;

deriving conditions of the patient and the environment from a plurality of signal features by means of a predefined mapping; and employing a temporal model to determine the most likely sequence of conditions in order to obtain accurate estimates of time duration of each condition and the frequency of condition changes, whereby attributes characterizing a patient's sleep quality from the time durations and frequency of condition changes can be derived.

18. The method of claim 13 comprising the further steps of:

using the sensed conditions of the patient to predict a likelihood that the patient will get out of bed or fall out of bed within a predetermined time period; and if the likelihood exceeds a threshold level, inform personnel disposed at the environment of the likelihood being above the threshold level.

19. The method of claim 13 comprising the further step of adjusting parameters of the treatment, the adjusting being performed between nightly said sleep activities.

20. The method of claim 13 comprising the further steps of:

using the sensed conditions of the patient to predict a likelihood that the patient will fall out of bed within a predetermined time period; and if the likelihood exceeds a threshold level, inform personnel disposed at the environment of the likelihood being above the threshold level.

* * * * *